United States Patent
Zimmermann

(10) Patent No.: US 6,465,226 B1
(45) Date of Patent: *Oct. 15, 2002

(54) PREPARING SMALL MICROCAPSULES CONTAINING HIGH CONCENTRATION OF CELLS OR TISSUE

(76) Inventor: Ulrich Zimmermann, Pfarrer-Frohlich-Strasse 17, D-97295, Waldbrunn (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/776,969
(22) PCT Filed: Jul. 25, 1995
(86) PCT No.: PCT/DE95/00972
§ 371 (c)(1), (2), (4) Date: Oct. 19, 1998
(87) PCT Pub. No.: WO96/03205
PCT Pub. Date: Feb. 8, 1996

(30) Foreign Application Priority Data

Jul. 26, 1994 (DE) .......... 44 26 396

(51) Int. Cl.⁷ .......... C12N 11/02; C12N 11/10; C12N 5/00; A61F 2/00
(52) U.S. Cl. .......... 435/177; 424/423; 424/93.7; 435/178; 435/182; 435/382; 435/395
(58) Field of Search .......... 435/174, 177, 435/178, 180, 182, 382, 395; 424/423, 93.7

(56) References Cited

U.S. PATENT DOCUMENTS

| | | | |
|---|---|---|---|
| 4,789,550 A | * 12/1988 | Hommel et al. | 424/493 |
| 4,801,529 A | * 1/1989 | Perlman | 435/5 |
| 5,521,079 A | * 5/1996 | Dorian et al. | 435/174 |
| 5,529,914 A | * 6/1996 | Hubbell et al. | 435/182 |

* cited by examiner

Primary Examiner—David M. Naff
(74) Attorney, Agent, or Firm—Edwin D. Schindler

(57) ABSTRACT

Biologically active substances such as cells or tissue are microencapsulated by methods that provide a high proportion of microcapsules containing a core of the biologically active substance as compared to microcapsules not containing the biologically active substance. Microcapsules are obtained having a maximum diameter of 300 micrometers and a high concentration of biologically active substance. A solution of encapsulating material such as alginate containing dispersed biologically active substance is passed through an inner channel of a two-channel spray nozzle to form droplets containing a core of the biologically active substance. Air flow from an outer channel of the nozzle causes the droplets to break off from the nozzle. Conditions of air flow and flow rate of solution are selected to obtain droplets having a volume of 1.5 to 4 times the volume of the biologically active substance that forms the core. The droplets are passed to a precipitation bath containing polycations such as barium ions where the encapsulating material is gelled to form microcapsules containing a core of the biologically active substance and empty microcapsules not containing the biologically active substance. The microcapsules are passed to a density centrifugal separator where the empty microcapsules are separated to obtain the microcapsules containing the biologically active substance. In an alternative method, an electrostatic field is used to separate the droplets from the nozzle.

6 Claims, No Drawings

PREPARING SMALL MICROCAPSULES CONTAINING HIGH CONCENTRATION OF CELLS OR TISSUE

BACKGROUND OF THE INVENTION

1. Technical Field of the Invention

The invention concerns the preparation of cells or dispersed active substances into high-concentration microcapsules. Microcapsules having a shell and a core for receiving the cells or dispersed active substances are prepared by various processes.

2. Description of the Prior Art

In medicine, there is the need to introduce living cells into the living human body in the form of islands, which are supplied there with nutrients and produce and secrete hormones missing because of disease-related disorders. Diabetes mellitus is named as an example, where the cells that produce insulin are obtained in the form of the so-called islands of Langerhans and introduced into the liver or the pancreas. In order to suppress the immune reactions it is necessary to provide these cells with a shell in the form of a capsule, whose core they then form. A similar need for encapsulating exists for insoluble but dispersed active substances.

Processes for micro-encapsulation are known. It is observed that in the case of capsules with a sufficiently large diameter, i.e. of over 600 μm, the reception of a core is possible without any problems. In contrast thereto, in the case of substantially smaller diameters, most of the capsules produced are without core, i.e empty. A further requirement results from the fact that the number of cells or pies of tissue to be introduced into the capsule as the core may not exceed a specific magnitude, as their inner regions would become necrotic due to deficient supply. In order to satisfy the body's need for the hormones generated by the cells to a sufficient extent, the volume or quantity of the core material to be introduced is specified. In the case of a diabetes disease, in order to produce the necessary quantity of insulin, more or less one million islands of Langerhans have to be implanted. If one were to use cores with a large diameter, a volume would have to be administered that exceeds considerably physical tolerance. Moreover, the exact placement of the cells, which is desirable per se, would almost prove impossible because of the high own space requirements. A further disadvantage consists therein that, owing to the large diffusion paths between the shell and the core, additional supply problems can occur. Because of the aforementioned reasons, the use of capsules with a large diameter, i.e. of over 600 μm, is ruled out in practice. The use of capsules with a small diameter does not offer a remedy in this respect, because the reduction of the original volume of a single capsule causes the proportion of the empty capsules, i.e. those not provided with a core, to increase significantly. In order to introduce the same quantity of cells or active substance, no tangible reduction in the total volume to be applied is obtained. In this case, a large proportion of empty and therefore medically inactive, but on the other hand non degradable material would be administered. In order to apply one million islands of Langerhans, an own volume of more or less 100 to 200 ml is necessary.

SUMMARY OF THE INVENTION

On this basis, it is the object of the invention to prepare cells or dispersed active substances into micro-encapsulated form, the proportion of microcapsules with cell and active substances being high while the own volume required is minimum.

In accordance with the invention, the task is solved herein that the air pressure or the diameter of the channels in the spray nozzle or the flow rate of the solution is set so that the droplet volume is 1.5 to 2 times the core volume. The microcapsules are then supplied to a density centrifugal separator with a density gradient adjusted so that he density of the used medium is higher than that of the empty microcapsules shells but lower than the density of the core-containing shells.

The central idea of the invention is, contrary to the aforementioned and known problems, to prepare capsules with a small diameter and then in a separation process to separate the empty and therefore biologically inactive capsules. Thus there is a concentration of the small core-containing capsules.

Capsules with a small diameter are prepared in that a spray nozzle provided with two channels is used, one channel, usually the outer one, being impinged by air, the inner one by a solution, which contains both the cells or the active substances as well as the shell material, i.e. the material for the capsule, in soluble form. The air flow causes droplets to break off at a specific size. The separating droplets reach a precipitation bath, where the shell is formed. By varying the air pressure correspondingly, selection of the diameter of the inner channel of the spray nozzle as well as the flow rate of the solution, droplets can be obtained whose volume comprises more or less 1.5 to 4 times the core volume. The core volume is specified by the staring material and the process used to obtain it. The shell surrounds the core directly and on all sides, without the retention of hollow volumes, so that the droplet size determines the volume of the capsule and, because of the defined, constant core volume, also the volume of the shell. The capsule diameter is a maximum of 200 μm. Larger diameters have longer diffusion paths which result in a deficient supply. Then, the reaction products, containing a multitude of empty capsules, are supplied to a density centrifuge in which the density gradient is adjusted so that the density of the medium is higher than that of the shell material but lower than the density of the core-containing shell. Thus, empty capsules are separated from those with a core.

DETAILED DESCRIPTION OF THE PREFERRED EMBODIMENTS

As an actual example the micro-encapsulation of the islands of Langerhans in barium alginate microcapsules is explained below.

To encapsulate islands of Langerhans, islands were removed from the pancreas of male Lewis rats (Charles River Wiga GmbH, Sulzfeld, Germany) having a body weight of over 350 g through intraductal inflation and collagenase digestion and washed twice with a solution which contained 0.9% NaCl and 10 mM morpholinoethane sulphonic acid (centrifuging 5 minutes at 16 g)

Sodium alginate (Manugel GHB, batch no. 548643-567853, Kelco International Ltd., London) was dissolved to 2.2% in distilled water. The pH-value of the alginate solution was set to 7.0–7.4 with 1 N NaOH. The alginate solution was sterilised by filtration through a cone-point attachable filter (0.2 μm; Renner, Darmstadt, Germany). Then 9 ml of the filter-sterilised alginate was mixed with 1 ml of 9% NaCl solution. In a milliliter of this solution approximately 1,000 of the isolated (as described above) islands of Langerhans were suspended. In order to splitter the island-containing alginate solution, a decor nozzle from the company Sata Ludwigsburg, Germany, was used. This consists of an hollow tube of narrow internal diameter (nozzle, internal diameter: 0.35 mm), through which the liquid is pressed, and a nozzle head which focus the airflow around the nozzle. Nozzle and nozzle head were fastened to a support on which were located the entrance for the compressed air and the alginate solution. By means of a controllable, motor-driven piston stroke the alginate solution was pressed out of an 1 ml injection needle through the inner channel of the spray nozzle (0.2 ml/min). With the aid of a compressed airflow small alginate droplets were separated from the nozzle. The compressed air was taken from the central compressed air supply of the institute, sterilised with a sterile filter with a pore width of 0.2 μm and with the aid of an admission pressure and a fine pressure controller set to a pressure of 40 mbar, the admission pressure being 1 bar.

From the nozzle, the alginate solution dropped into a Petri dish (diameter 10 cm), which contained 40 ml of a solution of 20 mM barium chloride, 0.72% NaCl and 10 mM morpholinoetane sulphonic acid (pH 7) (=precipitation bath). The distance between the nozzle and the precipitation bath was 10 cm. When the alginate solution dropped into the precipitation bath it immediately gelatinised and formed microcapsules having a diameter of approximately 10–350 μm. Most of the microcapsules created did not contain a core (i.e, no islands). After a dwell time of 10–15 minutes in the precipitation bath, the microcapsules were centrifuged (3 minutes at 170 g), washed three times with a 0.9% NaCl solution (centrifuging 3 minutes at 170 g) and suspended in 1 ml of an 0.9% NaCl solution.

The empty microcapsules were separated from the island-containing microcapsules through discontinuous density gradient centrifuging. Here different density solutions were superpositioned in a small tube in the centrifuge. These solutions were prepared by blending a Ficoll solution (Biochrom, Berlin, Germany, density 1.077 g/l at 20° C.) with RPMI 1640 liquid medium (Biochrom, Berlin, Germany). The solutions were pipetted, from bottom to top, into a small conical 15 ml centrifuge tube (Greiner, N ürtingen, Germany), starting with the highest Ficoll concentration: layer 1: 1 ml Ficoll solution, layer 2: 4 ml of a solution which contained 6 parts by volume of Ficoll solution and 4 parts by volume of RPMI 1640, layer 3: 1 ml of the suspension of the microcapsules in 0.9% NaCl. The small tubes were then centrifuged for 20 minutes at 2,700 g. Centrifuging was carried out at room temperature with the brake off. After centrifuging, the empty capsules were located at layer 2, whereas the island-containing capsules had migrated through layer 2 and collected at layer 1. Islands, not enclosed in an alginate capsule, were also able to migrate through layer 1 and were deposited on the base of the small tube. Through a hole in the small tube base, the solution was then drained off and captured in 0.5 ml portions. Portions containing microcapsules with islands were diluted with 20–30 ml of 0.9% NaCl and the is island-containing microcapsules separated off by centrifuging (20 minutes, 100 g) for further experiments. This process resulted in island-containing barium alginate microcapules with an average volume of $5.7 \pm 2.2 \times 10^6$ μm$^3$. On the other hand, the average volume of the non-encapsulated islands was $3.3 \pm 1.4 \times 10^6$ μm$^3$.

More than 90% of the microcapsules last obtained contained an island. From the originally used islands 72% were recovered in micro-encapsulated form.

As a result one obtains a multitude of capsules of small diameter, which, owing to the separation process, consistently contain a medically active core. Their diameter is slightly larger than the biologically active capsule core so that the volume to be administered minimises, i.e., is only marginally larger than the biologically active and utilisable core material that necessarily must be introduced. Thus, the required quantity of biologically active material can be restricted to a volume of 5 to 10 ml, which can be placed selectively and accurately owing to the low own weight. Moreover, the substances acquired according to the invention are also suitable in other areas, eg., for use in bioreactors, to create high performance densities in significant scales.

Besides the nozzles described, impinged by air and solution, other methods to create the micro-encapsulated cells or active substances are conceivable In the electrostatic preparation of microcapsules (electrostatic droplet generator), a suspension of the material to be encapsulated, ie. the core material, is prepared in an aqueous solution of the capsule material and dropped, by a nozzle, into a precipitation bath. The latter contains polyvalent cations, which trigger the gelling of the capsule material. Decisive is to apply an electrostatic field between the nozzle and the precipitation bath, which acts in the direction of fall. This provides the droplet emerging at the nozzle with a high electrostatic charge and, owing to the opposing, charged precipitation bath, is subject to forces of attraction which cause an early separation of the droplet. Thus comparatively small droplets are created. In contrast to the process first described, where droplet separation is aided by an airflow, here electrostatic forces cause early separation.

The following describes the example of the micro-encapsulation of islands of Langerhans in barium alginate microcapsules by electrostatic droplet formation:

To encapsulate islands of Langerhans, islands were removed from the pancreas of male Lewis rats (Charles River Wiga GmbH, Sulzfeld, Germany) having a body weight of over 350 g through intraductal inflation and collagenase digestion and washed twice with a solution which contained 0.9% NaCl and 10 mM morpholinoethane sulphonic acid (centrifuging 5 minutes at 16 g).

Sodium alginate (Manugel GHB, batch no. 548643-567853, Kelco International Ltd., London) was dissolved to 2.2% in distilled water. The pH-value of the alginate solution was set to 7.0–7.4 with 1 N NaOH. The alginate solution was sterilised by filtration through a cone-point attachable filter (0.2 μm; Renner, Darmstadt, Germany). Then 9 ml of the filter-sterilised alginate was mixed with 1 ml of 9% NaCl solution. In a milliliter of this solution approximately 1,000 of the isolated (as described above) islands of Langerhans were suspended. The alginate solution was filled into an 1 ml injection needle to which a 22 G injection needle was connected. In order to splitter the island-containing alginate solution, an electrostatic droplet generator of the following design was used: The injection needle was connected to the negative output of an high voltage pulse generator via a connecting cable. Exactly 1 cm below the injection needle a Petri dish (diameter 10 cm) was located, which contained 20 ml solution of 20 mM barium chloride, 0.72% NaCl and 10 mM morpholinoethane sulphonic acid (pH 7) (=precipitation bath). The solution in the Petri dish was connected to the positive output of the pulse generator. By means of a controllable, motor-driven piston stroke, the alginate solution was pressed from the needle at a speed of 0.2 ml/min. At the same time, via the high voltage generator, every 50 msec pulses of a field strength of 12 kV and a duration of 2 msec were applied. Thus the finest alginate droplets were separated from the needle point, falling into the precipitation bath. On dropping into the precipitation bath, the alginate solution immediately gelatinised and formed microcapsules with a diameter of approximately 10–400 μm. Most of the microcapsules created did not contain a core (i.e no islands). After a dwell time of 10–15 minutes in the precipitation bath, the microcapsules were centrifuged (3 minutes at 170 g), washed three times with a 0.9% NaCl solution (centrifuging 3 minutes at 170 g) and suspended in 1 ml of an 0.9% NaCl solution.

The empty microcapsules were separated from the island-containing microcapsules by discontinuous density gradient centrifuging. Here solutions of different density were superpositioned in a small tube of the centrifuge. These solutions were prepared by blending a Ficoll solution (Biochrom, Berlin, Germany, density 1.077 g/l at 20° C.) with RPMI 1640 liquid medium (Biochrom, Berlin, Germany). The solutions were pipetted, from bottom to top, into a small conical 15 ml centrifuge tube (Greiner, Nürtingen, Germany), starting with the highest Ficoll concntration: layer 1: 1 ml Ficoll solution, layer 2: 4 ml of a solution which contained 6 parts by volume of Ficoll solution and 4 parts by volume of RPPMI 1640, layer 3: 1 ml of the suspension of the microcapsules in 0.9% NaCl. The small tubes were then centrifuged for 20 minutes at 2,700 g. Centrifuging was carried out at room temperature with the brake off. After centrifuging, the empty capsules were located at layer 2, whereas the island-containing capsules had migrated through layer 2 and collected at layer 1. Islands, not enclosed in an alginate capsule, were also able to migrate through layer 1 and were deposited on the small tube base. Through a hole in the small tube base, the solution was then drained off and captured in 0.5 mil portions. Island-containing microcapsule portions were diluted with 20–30 ml of 0.9% NaCl and the island-containing microcapsules separated off by centrifuging (20 minutes, 100 g) for further experiments. This process resulted in island-containing barium alginate microcapsules with an average volume of $5.7 \pm 2.2 \times 10^6$ μm$^3$. On the other hand, the average volume of the non-encapsulated islands was $3.3 \pm 1.4 \times 10^6$ μm$^3$. More than 90% the microcapsules obtained after the last step contained an island. From the originally used islands 72% were recovered in micro-encapsulated form.

In the still possible process of emulsification, likewise first a suspension of be material to be encapsulated (cells, active substances) is prepared in the aqueous solution of the shell material. This aqueous suspension is then introduced into an oil bath or into a different solution which is not mixable with water. By means of intensive agitation a water-in-oil emulsion is created, whose droplet size depends on the intensity of the agitation process. The more intensive the agitation process, the smaller the droplet diameter. In order to trigger gelinatisation of the shell material, the polyvalent cations are then introduced into the bath.

In a further embodiment, it is seen as practical, above and beyond the separation of the empty capsules described above, to additionally separate pure core material from the fraction that is introduced into the capsule and designed solely for application. Here an additional subordinate separation stage is performed in the direction of action of the centrifugal force in which the densities of the individual regions are as follows. Starting from the rotation axis, the location of the sample, a density is selected which is higher than that of the empty capsule, but lower than that of the core-containing capsule or the core alone. In the next stage, a density is selected which is lower than that of the core but higher than that of the core-containing capsule. In such a procedure not only the empty capsules but also the very cores are separated off so that the actually desired and intended material, namely capsules with cell core, is available. It can be obtained from the central region from the perspective of a radial direction.

The density gradient across the radius can be steady and continuous. However, it is preferred to effect the transition between the regions of differing densities step-wise. Then the capsules it is intended to obtain are highly concentrated in the region of the step concentration so that a maximum yield is achieved in the subsequent extraction.

As shell material, alginate gels or thermotropic or ionotropic gels are proposed. The substances termed 'alginate' are formed by chain copolymers, whose elements are mannuronic and guluronnic acids. By way of contrast, alginate gels are the chain copolymers of alginate linked in a netted structure. Gels are termed thermotropic if the gel formation is induced through a temperature change; ionotropic gels on the other hand are formed by a change of the ion concentration, where the ion concentration that induces the gel formation can differ depending on the structure of the gel. Thermotropic gel examples are agar, agarose, gelatin and the like. Examples of ionotropic gels are: gellan, carragheen and cellulose sulphate.

Core material usually comprises living cells, especially those producing hormones, but also dead ones, or dispersed active substances. Pursuant to customary terminology, dead cells are deemed to be those ones whose cell walls have been made permeable. The enzymes in the cells are thus able to interact unimpaired with their environment and to carry out the desired transformations. In contrast, with living cells, i.e. with closed cell membranes, the conversion would only be able to occur very slowly, if at all. The term 'active substances' is, within the meaning of the invention, to be understood generally and encompasses all conceivable types of chemical compounds that show biological action. These include especially all pharmacologically active substances, i.e. those that act upon the human organism, as well as those products acting on plants (herbicides) and also on animals (acting in veterinary medicine or pesticides).

In order to cross-link and form the shells in the precipitation bath, bivalent barium ions Ba++ and other bivalent or trivalent cations are used. This applies especially also when alginate is used as the shell material.

In the use of alginate as a shell material, it is known in the state-of-the art to introduce polycations into the precipitation bath. An alginate-polycation-complex is then created of two-layered shell structure because the alginate net is covered by one of polycations. Here the polycations bond both the mannuronic and guluronnic acids. The significantly disadvantageous result is a narrow mesh aperture and a high density. The decisive disadvantage is that the immune system recognises this structure as an antigen and triggers corresponding reactions.

The present invention differs therefrom fundamentally because first a single-layer shell structure is obtained, which is to be denoted an alginate-cation-complex from the structural perspective. Thereby the cations bind the mannuronic and guluronnic acids. A network arises in which the alginate of sufficiently low density is developed. The density of the shell is thus substantially lower than that of the core, which in the following separation proves a decisive advantage. The shell arises through a binding of macromolecules, which comprise polymers from the two monomers mannuronic and guluronnic acid. Thus the single-layered structure arises.

The density of the core is always higher than the density of the shell, because the nutrients and active substances must diffuse through. Owing to the later separation, a large difference in the density of the shell and core is advantageous. Although the density of the core is subject to fluctuations, the density of the shell must always be selected higher. In the case of the cation binding according to the invention, a comparatively low density shell is obtained, which is to be valued as an advantage. On the other hand, the density of the shell must not be selected so low that the macromolecules of the antibodies can diffuse through. Permeability is only to be given for the low-molecular nutrients and active substances. It follows that a small mesh width is required, which may not exceed a specific size. The mesh width is set via the alginate (in the state-of-the-art by selecting the corresponding polycation). Thus the density of the shell must be less than that of the core, on the other hand selected large enough that a sufficiently small mesh width obtains which prevents the diffusion through of antibodies.

The present invention claims a microcapsule, inside of which cells or dispersed active substances are accommodated as a core. Its exterior diameter is a maximum of 200 to 300 μm. With larger diameters, the diffusion paths are too long so that the cores do not receive sufficient nutrients. The core is surrounded on all sides and directly, i.e. without any hollow spaces located therebetween, by the shell. The core volume is specified by the material to be introduced and its dimensions are determined by the respectively applied preparation method. The larger the set droplet size, the larger the shell volume. Processes to prepare this kind of microcapsule have already been explained above With the use of alginates with cations, a shell of macromolecules is obtained in which polymers are cross-linked through cations. These polymers are created from monomers of mannuronic and guluronnic acids.

What is claimed is:

1. A method for preparing microcapsules containing a core of a biologically active substance comprising cells or tissue and having a maximum diameter of 300 micrometers, comprising the steps of:

passing a solution of a soluble gellable encapsulating material containing a dispersed biologically active substance comprising cells or tissue through an inner channel of a two-channel spray nozzle having said inner channel and an outer channel for air flow for forming droplets containing a core of the biologically active substance;

causing the droplets to separate from the two-channel spray nozzle by air flow from the outer channel, wherein air pressure in the outer channel, diameter of the inner channel, diameter of the outer channel or flow rate of the solution containing the dispersed biologically active substance through the inner channel is selected for obtaining droplets having a volume of 1.5–4 times the volume of the biologically active substance that forms the core of a microcapsule;

passing the droplets to a precipitation bath containing a solution of bivalent barium cations where the soluble gellable encapsulating material is gelled by the bivalent barium cations cross-linking the gellable encapsulating material to form microcapsules containing the biologically active substance and microcapsules not containing the biologically active substance, wherein said microcapsules have a maximum diameter of 300 micrometers; and, supplying the microcapsules to a density centrifugal separator where a medium having a density gradient adjusted to a density higher than the density of microcapsules not containing the biologically active substance and a density lower than the density of the microcapsules containing the biologically active substance separates the microcapsules not containing the biologically active substance for obtaining the microcapsules containing a core of the biologically active substance and having a maximum diameter of 300 micrometers.

2. The method of claim 1, wherein the biologically active substance comprises tissue.

3. The method of claim 1, wherein the precipitation bath contains barium chloride to provide said bivalent barium cations.

4. A method for preparing microcapsules containing a core of a biologically active substance comprising cells or tissue and having a maximum diameter of 300 micrometers, comprising the steps of:

passing a solution of a soluble gellable encapsulating material containing a dispersed biologically active substance comprising cells or tissue through an inner channel of a two-channel spray nozzle having said inner channel and an outer channel for air flow for forming droplets containing a core of the biologically active substance;

causing the droplets to separate from the two-channel spray nozzle by applying an electrostatic field between said two-channel spray nozzle and a precipitation bath, while adjusting field strength of the electrostatic field for obtaining droplets having a volume of 1.5–4 times the volume of the biologically active substance that forms the core of a microcapsule;

passing the droplets to the precipitation bath containing a solution of bivalent barium cations where the soluble gellable encapsulating material is gelled by the bivalent barium cations cross-linking the gellable encapsulating material to form microcapsules containing the biologically active substance and microcapsules not containing the biologically active substance, wherein said microcapsules have a maximum diameter of 300 micrometers; and, supplying the microcapsules to a density centrifugal separator where a medium having a density gradient adjusted to a density higher than the density of microcapsules not containing the biologically active substance and a density lower than the density of the microcapsules containing the biologically active substance separates the microcapsules not containing the biologically active substance for obtaining the microcapsules containing a core of the biologically active substance and having a maximum diameter of 300 micrometers.

5. The method of claim 4, wherein the biologically active substance comprises tissue.

6. The method of claim 4, wherein the precipitation bath contains barium chloride to provide said bivalent barium cations.

* * * * *